United States Patent [19]

Tarlov

[11] Patent Number: 5,514,501
[45] Date of Patent: May 7, 1996

[54] PROCESS FOR UV-PHOTOPATTERNING OF THIOLATE MONOLAYERS SELF-ASSEMBLED ON GOLD, SILVER AND OTHER SUBSTRATES

[75] Inventor: Michael J. Tarlov, Washington, D.C.

[73] Assignee: The United States of America as represented by the Secretary of Commerce, Washington, D.C.

[21] Appl. No.: 255,961

[22] Filed: Jun. 7, 1994

[51] Int. Cl.[6] .................. G03F 7/00; G03C 5/16
[52] U.S. Cl. .................. 430/5; 430/311; 430/315; 430/322; 430/324; 430/396; 427/377; 427/387; 427/539
[58] Field of Search .................. 430/5, 311, 315, 430/322, 324, 396; 427/377, 387, 539

[56] References Cited

U.S. PATENT DOCUMENTS

| | | | |
|---|---|---|---|
| 3,940,912 | 3/1976 | Buchner | 423/658.2 |
| 4,410,562 | 10/1983 | Nemoto et al. | 427/54.1 |
| 4,477,326 | 10/1984 | Lin | 522/21 |
| 4,640,940 | 2/1987 | Jacobine et al. | 522/99 |
| 4,715,929 | 12/1987 | Ogawa | 216/48 |
| 4,948,712 | 8/1990 | Inoue et al. | 430/409 |
| 4,964,972 | 10/1990 | Sagiv et al. | 204/418 |
| 4,994,358 | 2/1991 | Deguchi et al. | 430/547 |
| 5,077,085 | 12/1991 | Schnur et al. | 427/98 |
| 5,079,600 | 1/1992 | Schnur et al. | 257/750 |
| 5,120,569 | 6/1992 | Zupanic et al. | 427/43.1 |
| 5,126,007 | 6/1992 | Shmulovich | 216/48 |
| 5,220,030 | 6/1993 | Deaton | 548/105 |
| 5,223,117 | 6/1993 | Wrighton et al. | 204/415 |

Primary Examiner—Kathleen Duda
Attorney, Agent, or Firm—Evenson, McKeown, Edwards & Lenahan

[57] ABSTRACT

A process for creating a two dimensional spacial distribution pattern of different thiolate molecules on a substrate by illuminating a surface of a self-assembled monolayer of a first thiolate compound in the presence of oxygen with high frequency electromagnetic radiation distributed according to a desired pattern, and subsequently immersing the illuminated substrate in a solution of a second thiolate compound so that molecules of the first thiolate compound in illuminated areas of the monolayer are exchanged for molecules of said second thiolate compound; and a patterned biomolecular composite formed of a substrate which forms a self-assembled thiolate monolayer when immersed in a solution of a thiolate forming compound, a thiolate monolayer deposited on the substrate and composed of patterned areas of first and second thiolate compounds, respectively, the first thiolate compound having an affinity for specifically or non-specifically adsorbing a biological molecule, and the second thiolate compound having essentially no affinity for the biological molecule, and at least one biological material adsorbed in a corresponding pattern on the patterned areas of the first thiolate compound in the thiolate monolayer.

15 Claims, 6 Drawing Sheets

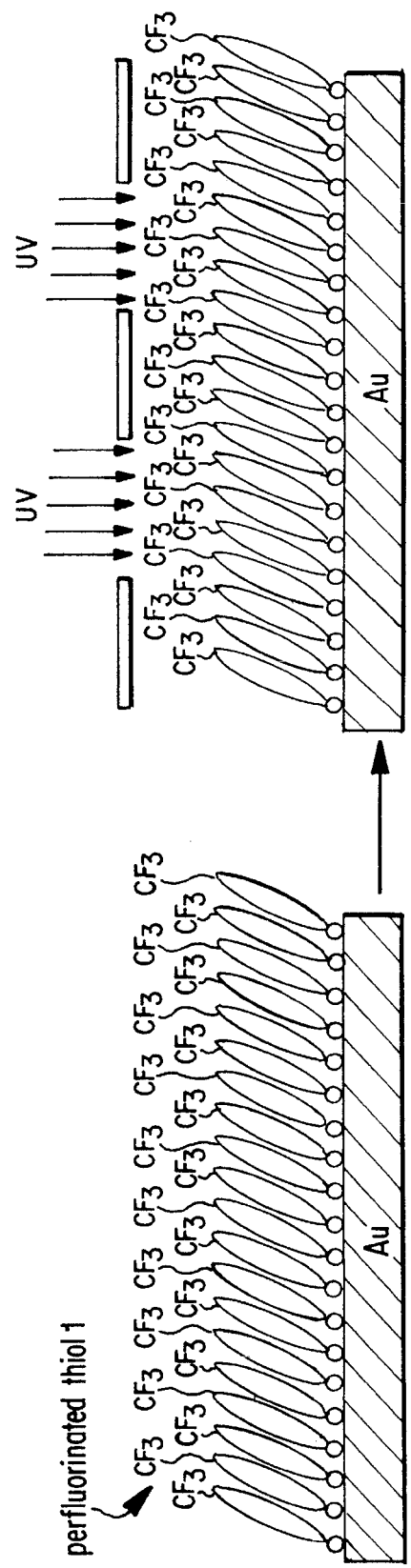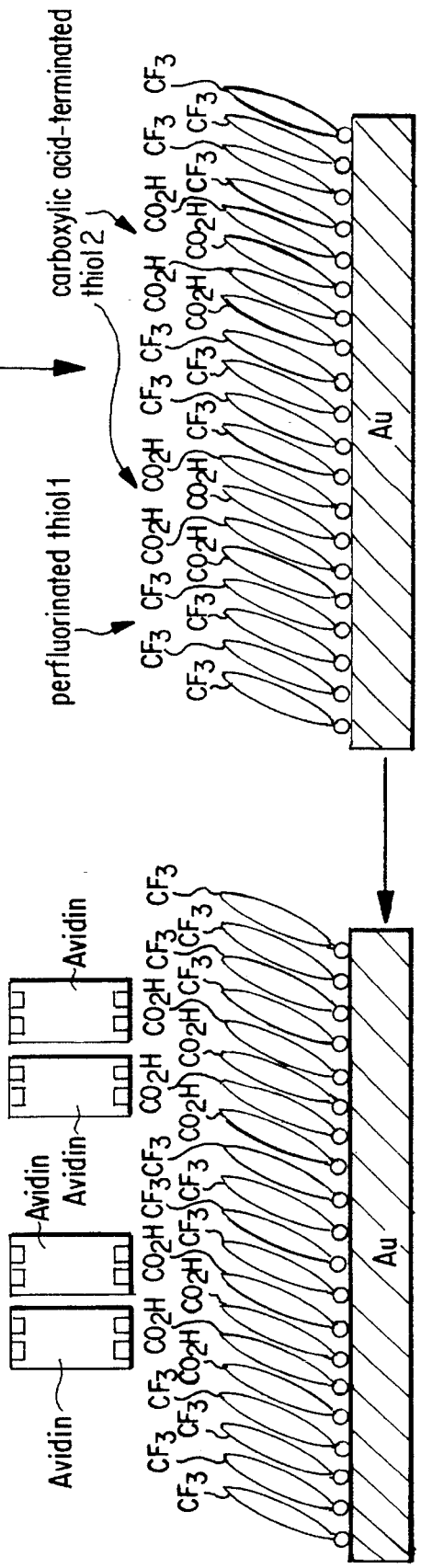

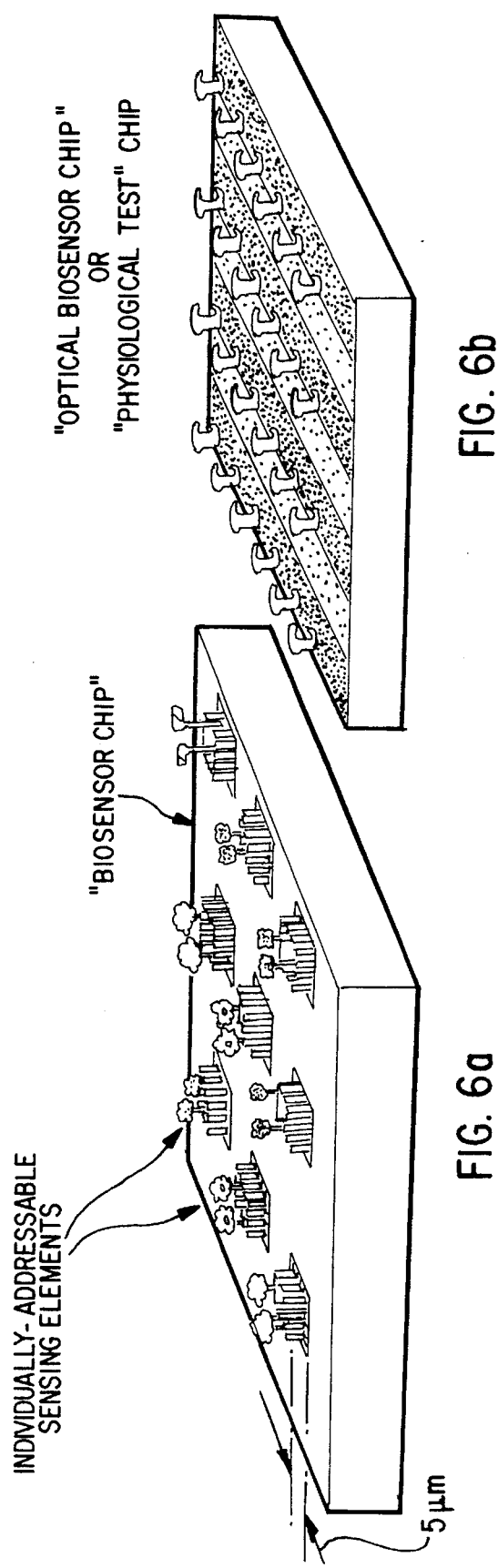

SIMS Images of Avidin Adsorbed on a Patterned Perfluoro- and Carboxy Alkanethiol SAM on Au

PROCESS FOR UV-PHOTOPATTERNING OF THIOLATE MONOLAYERS SELF-ASSEMBLED ON GOLD, SILVER AND OTHER SUBSTRATES

BACKGROUND OF THE INVENTION

The present invention relates to a photopatterning process for controlling the two dimensional spatial distribution of molecules in thiolate self-assembled monolayers ("SAMS"), particularly alkylthiolate self-assembled monolayers, on gold, silver and other substrates.

Precise control of the spatial position of the thiol compound molecules on a surface would permit manipulation of the chemical and physical properties of selected areas of the surface to bind inorganic, organic, and biological molecules and species. The ability to bind biological species such as proteins, enzymes, DNA and cells at known locations on surfaces could be important for a variety of technologies including biosensing, immunoassay diagnostics, DNA probe diagnostics and sequencing, pharmacological and toxicological testing, and cell growth studies. For example, in the area of biosensing, the ability to pattern and immobilize multiple proteins on surfaces would allow the construction of miniaturized, multi-analyte sensors capable of operating in blood vessels or on a single cell. In the area of DNA sequencing, the ability to immobilize DNA probes on surfaces with $\leq 10$ micrometer spacing would be a key step in the fabrication of a new generation of miniaturized DNA sequencers supported on micro-chips. The same monolayer patterning process could also be used to lithographically pattern the underlying substrate (gold and silver) through the use of chemical etching reactions to form individually addressable micro-electrodes that would be useful for many chemical sensing and diagnostic applications.

Two processes are currently known for patterning alkylthiol monolayers on compatible substrates. The first is a mechanical method such as disclosed by N. L. Abbott, J. P. Folkers, and G. M. Whitesides in *Science* 257 (1992) at pp. 1380–1382, whereby portions of the SAM are physically removed by impressing a scalpel or carbon fibers across or on the SAM sample. This method suffers from the disadvantages, however, that the use of physical force may deform and damage the sample and/or the expensive pattern mask. The second process is a photolithographic method disclosed in Frisbie et al., *Journal of Vacuum Science and Technology A*, Vol. 11, pp. 2368–72 (1993). This process requires that a specific photo-active functional group (an aryl azide) be incorporated in the alkylthiol molecules, and thus is not generally applicable to other alkylthiols.

SUMMARY OF THE INVENTION

Accordingly, an object of the present invention is to provide a photopatterning process for precisely regulating the two dimensional distribution of surface molecules in a SAM.

Another object of the invention is to provide a precise process for photopatterning SAMs which permits the formation of closely spaced features (line spacing less than 100 micrometers) therein.

Yet another object of the invention is to provide a photopatterning method that does not require physical contact with the sample, and thus does not deform the substrate.

Still another object is to provide a process that does not require the presence of a photo-active pendant group and is therefore applicable to SAMs comprised of molecules of any compound capable of forming a thiolate SAM.

A further object of the invention is to provide a patterned biomolecular composite in which a biological material is adsorbed on a substrate in a controllable patterned arrangement.

These and other objects of the invention are achieved by providing a process for creating a pattern comprising a two dimensional spacial distribution of thiolate compound molecules in a self-assembled monolayer formed on a substrate comprising the steps of illuminating a surface of a self-assembled monolayer of a first thiolate compound in the presence of oxygen with high frequency electromagnetic radiation distributed according to a desired pattern; and immersing the substrate in a solution of a compound capable of producing a second thiolate compound, whereby molecules of the first thiolate compound in illuminated areas of the monolayer are exchanged for molecules of the second thiolate compound.

In accordance with a further aspect of the invention, the objects are also achieved by providing a patterned biomolecular composite comprising a substrate capable of forming a self-assembled thiolate monolayer when immersed in a solution of a compound capable of forming a thiolate compound; a thiolate monolayer deposited on the substrate, the thiolate monolayer comprising patterned areas composed of first and second thiolate compounds, respectively, wherein the first thiolate compound has an affinity for specifically or nonspecifically adsorbing a biological molecule, and the second thiolate compound has essentially no affinity for the biological molecule; and at least one biological material adsorbed in a corresponding pattern on the patterned areas of the thiolate monolayer composed of the first thiolate compound.

The patterning method according to the invention has been derived from two observations. The first observation is that when adsorbed alkylthiolate ($RS^-$) molecules are irradiated with ultraviolet (UV) light in air, the molecules in the monolayer are oxidized to the corresponding alkylsulfonate ($RSO_3^-$) molecules. The second observation is that alkylsulfonates are weakly bound to substrate surfaces, and are thus easily displaced from the SAM by subsequent immersion of the sample in a solution of a compound capable of forming a thiolate compound, such as an alkylthiol solution, a dialkyl sulfide solution or a dialkyl disulfide solution. The photopatterning method of the invention makes use of these two observations in combination.

A thiolate monolayer is first self-assembled on a gold, silver or other suitable substrate surface. A pattern of sulfonate molecules is then formed in the SAM by UV irradiation in air (e.g. using a high pressure mercury lamp) through a mask. The mask can be placed directly on the sample or can be imaged on the sample using appropriate optics. The UV light in the presence of oxygen causes a photo-oxidation reaction to occur, whereby the thiolate headgroups are converted to sulfonate functional groups. After UV exposure, the sample is then immersed in a dilute solution of a different thiol compound. The sulfonate molecules in the exposed areas of the original SAM are displaced, incorporating the second type of thiolate compound into the monolayer. This process results in a single monomolecular film composed of molecules of two types of thiolate compounds in a pattern determined by the mask.

Pattern features in the SAMs of approximately 10 micrometers have been demonstrated on gold and silver substrates using the process according to the invention.

X-ray photoelectron spectroscopy (XPS) and secondary ion mass spectrometry (SIMS) imaging have been used to characterize the UV-irradiated and exchanged monolayers. XPS spectra of the S 2p region indicate the formation of sulfonate species upon UV irradiation and their displacement by thiolates following immersion. SIMS images of photopatterned and thiol-exchanged SAMs confirm the existence of two molecularly distinct assemblies with faithful reproduction of the mask pattern and resolution of features as small as 15 μm.

Any substrate on which a thiol SAM will form may be used in the invention. The substrate may take the form of a foil, a wafer or a chip of the desired material. Alternatively, particularly with precious metal substrate materials, it is desirable to use as the substrate a layer of substrate material deposited on a base material by any known deposition process. Suitable substrate materials include gold, silver, copper, platinum, iridium, palladium, rhodium, mercury, osmium, ruthenium, gallium arsenide, indium phosphide, mercury cadmium telluride, and the like. Gold and silver are particularly preferred.

The light pattern to which the thiol monolayer is exposed may be generated using any suitable source of electromagnetic radiation which will promote the oxidation in oxygen or air of a thiol group to a sulfonate group. Ultraviolet light of any wavelength or even x-ray radiation may be used. Particularly good results have been obtained using a mercury lamp as the light source.

The exposure and exchange steps may advantageously be carried out at ambient temperature, although higher or lower temperatures may be used. The exposure time required to oxidize the thiolate groups to sulfonate groups will vary depending on the layer density or thickness, the oxygen concentration and the intensity and/or wavelength of the applied radiation. For typical mercury vapor lamp, exposure times in air of 15 minutes to 1 hour or more may be used with good results. For any given case, persons skilled in the art can readily determine appropriate exposure times by simple testing.

The exchange time is not critical. Immersion times of as little as one minute or as long as an hour or more have yielded satisfactory results. Unduly extended immersion times for the exchange or developing step are preferably avoided, however, since they may increase the likelihood that the original thiolate compound in the unexposed regions may undergo exchange with the new thiolate compound of the exchange solution.

Exchange in unexposed regions can be limited by removing sulfonate species prior to immersing the exposed substrate in the solution of the new thiolate compound. Removal may be effected by means of a solvent such as ethanol, methanol, water, acetone, dimethyl sulfoxide, hexane, tetrahydrofuran or dimethylformamide, or by laser treatment or ion bombardment techniques.

Other objects, advantages and novel features of the present invention will become apparent from the following detailed description of the invention when considered in conjunction with the accompanying drawings.

BRIEF DESCRIPTION OF THE DRAWINGS

FIGS. 5a–5d depict the steps of the process according to the invention applied to control the placement of biological molecules on a surface;

FIGS. 6a and 6b are structural depictions of patterned biomolecular films formed according to the invention.

DETAILED DESCRIPTION OF PREFERRED EMBODIMENTS

Figure 1:
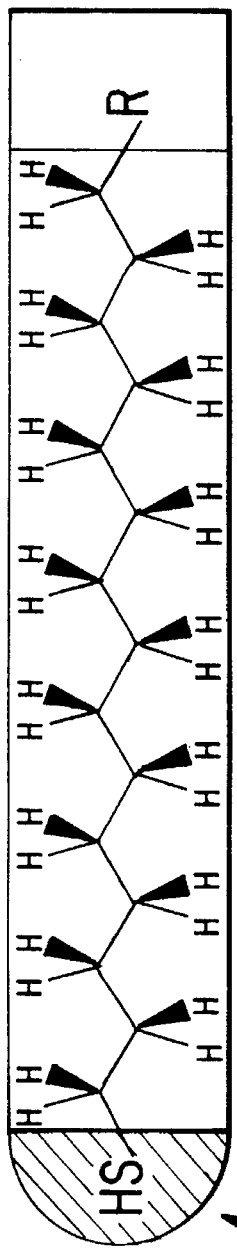
FIG. 1 is a structural depiction of a single alkylthiol molecule.

Thiolate self-assembled monolayers (SAMs) are well-defined monomolecular films that offer tremendous flexibility in tuning the chemical and physical properties of surfaces and interfaces. Such films can be formed from thiol molecules such as omega-substituted alkanethiols and disulfides. For example, alkylthiols or thiophenols may be used. Alkylthiol molecules, illustrated structurally in FIG. 1, correspond to the general formula $R-(CH_2)_n-SH$, where SH is the sulfur or thiol head group, n may represent any desired integer depending on the desired character of the layer to be formed, and R represents the terminal functional group (e.g., HOOC—, $-CH_3$, $-NH_2$, $CF_3$, halogen, etc.). Typically n will range from 0 to 21. The group R may be any functional group which will confer a desired character on the SAM, depending on the intended use.

Other types of compounds which are capable of producing alkylthiolate monolayers and are useful in the invention include dialkyl sulfides and dialkyl disulfides.

Dialkyl sulfides correspond to the general formula $R(CH_2)_m S(CH_2)_n R'$ where R and R' may be any terminal functional groups, and m and n represent any desired integers. Typically m and n will range from zero to 21. Either symmetrical or asymmetrical dialkyl sulfides may be used. Examples of symmetrical dialkyl sulfides include $[CH_3(CH_2)_n]_2 S$, $[HOOC(CH_2)_n]_2 S$, $[F(CF_2)_m (CH_2)_n]_2 S$ and the like where m and n have the meanings given above. Examples of asymmetrical dialkyl sulfides include $CH_3(CH_2)_9 S(CH_2)_{10} COOH$, $CH_3(CH_2)_5 S(CH_2)_{10} COONa$ and $CH_3(CH_2)_{15} S(CH_2)_{15} COOH$ and the like.

Examples of dialkyl disulfide compounds include symmetrical dialkyl disulfides such as $[S(CH_2)_n OH]_2$, $[S(CH_2)_n CH_3]_2$, $[S(CH_2)_n Br]_2$, $[S(CH_2)_n COOH]_2$ and the like, and asymmetrical dialkyl disulfides corresponding to the formula $R(CH_2)_m S-S(CH_2)_n R'$ where R and R' may be any terminal functional groups as describe above, and m and n have the meanings given above, with the proviso that R and R' may only be the same if m and n are different, and m and n may only be equal if R and R' are different.

The foregoing lists are merely representative examples, and there many other compounds which could be used in the invention. The important characteristic is the ability to form a thiolate monolayer on a substrate.

A monolayer is formed by immersing an appropriate substrate (such as gold, silver, copper, etc.) into a dilute solution of a compound capable of forming a thiolate group, such as an alkylthiol. For convenience in discussion, the following description will refer specifically to alkylthiol compounds, but it should be understood that any compound which is capable of forming a thiolate monolayer may be used in the invention.

Figure 2:
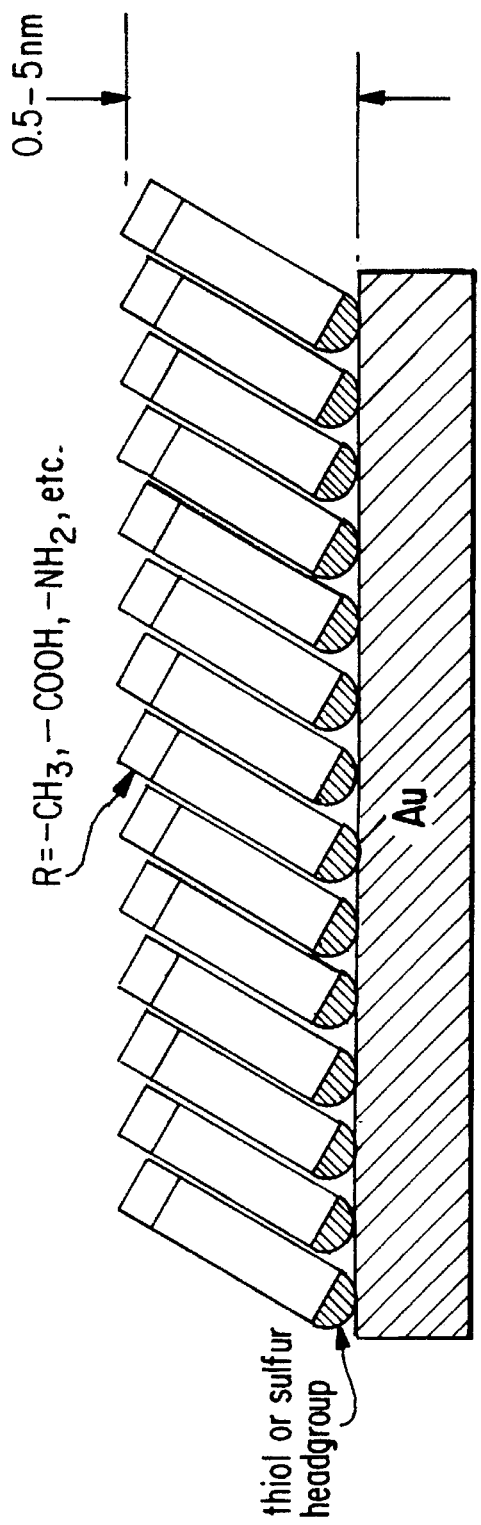
FIG. 2 is a cross sectional view of a self assembled monolayer (SAM) deposited on a gold substrate.

The alkylthiol molecule adsorbs strongly through the sulfur (SH) head group to the substrate surface to form densely packed monolayer films with fully extended hydrocarbon [—$(CH_2)_n$—] chains, as shown in FIG. 2. It is believed that upon chemisorption on the substrate, the thiol head group loses its hydrogen to form a thiolate. Because the alkylthiolate molecules are anchored to the gold or silver by the sulfur head, the exposed surface of the monolayer is comprised of the terminal functional group R. By varying the identity of the R group, the surface properties of the SAMs can be tailored for a particular application.

Figure 3A:
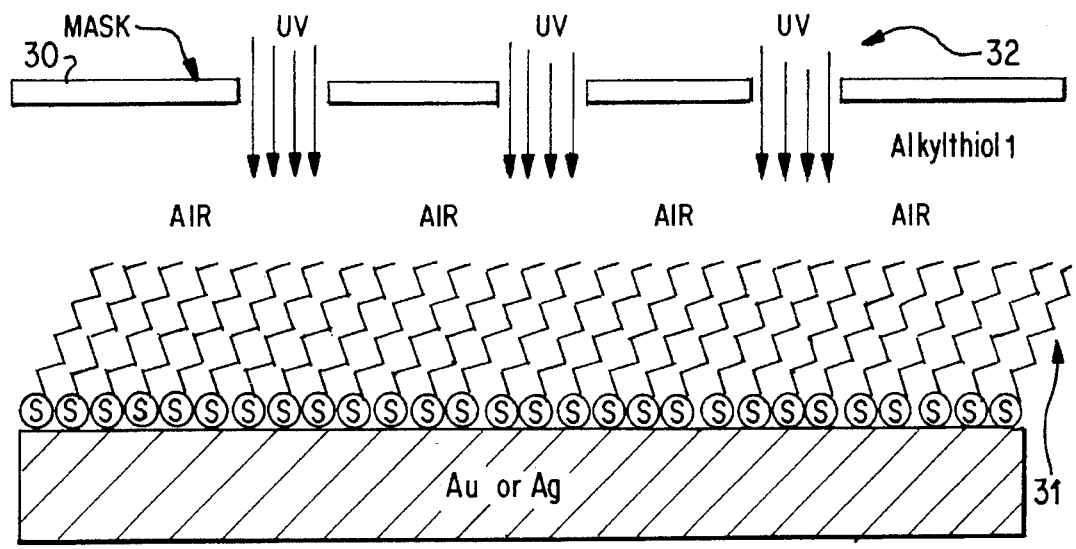
FIGS. 3a–3c depict various steps of the photopatterning process according to the invention.
Figure 3B:
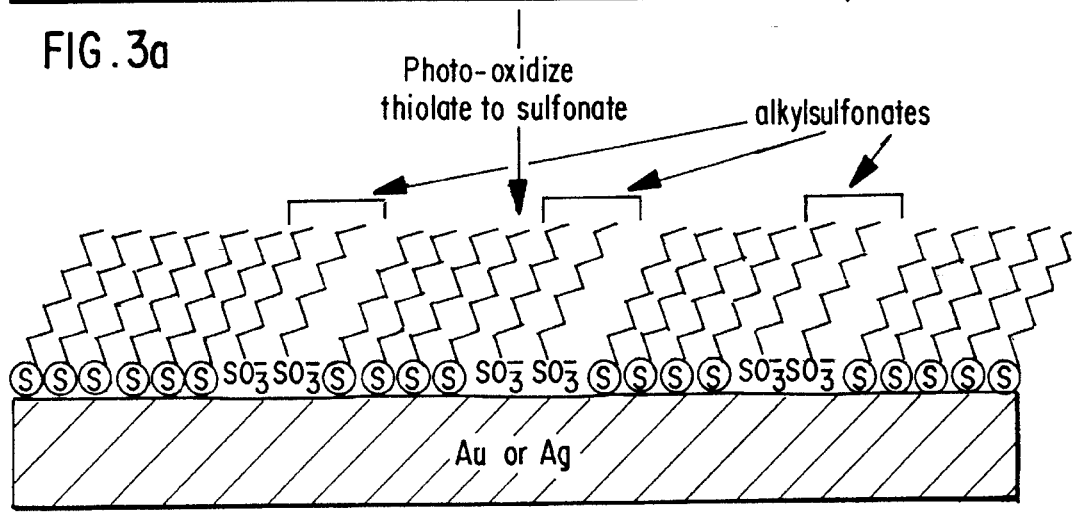
Figure 3C:
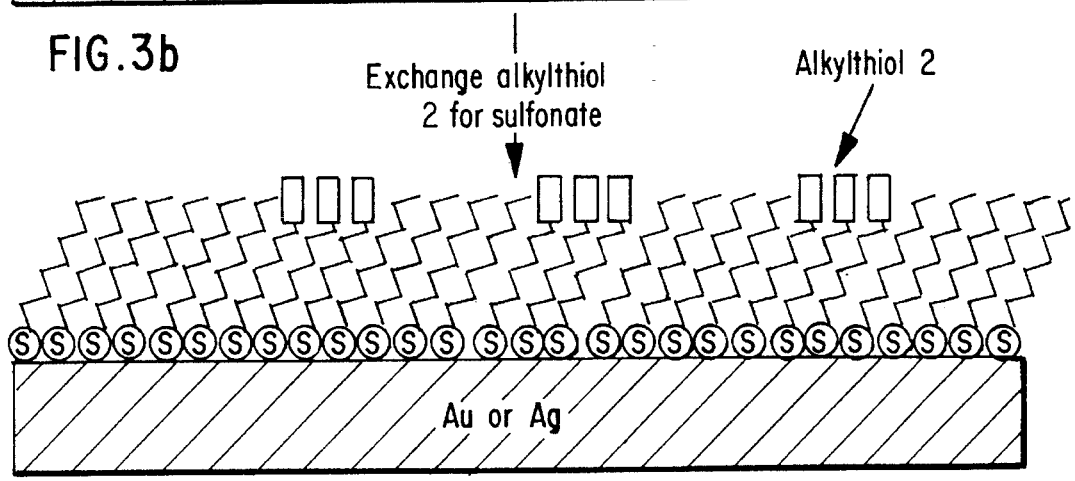

FIGS. 3a through 3c illustrate the structure of the substrate and SAM as the respective steps of the process according to the invention are performed. In FIG. 3a, a mask element 30 is placed over the SAM 31, and ultraviolet light 32 is radiated onto the surface of the SAM through openings in the mask, which are arranged in a desired pattern, while the SAM is also exposed to air, oxygen, nitrous oxide, or other oxidizing gases. As shown in FIG. 3b, in the exposed portions of the SAM, irradiation with ultraviolet light in air causes the alkylthiolate to be oxidized to the corresponding alkylsulfonate, which is weakly bound to the substrate surface. Following irradiation, the substrate is immersed in a solution of a different alkylthiol, and the weakly bound alkylsulfonates are displaced and exchanged for the second alkylthiol molecules in the desired pattern, as shown in FIG. 3c. In the unexposed areas, the first alkylthiolate is retained.

Figure 4:
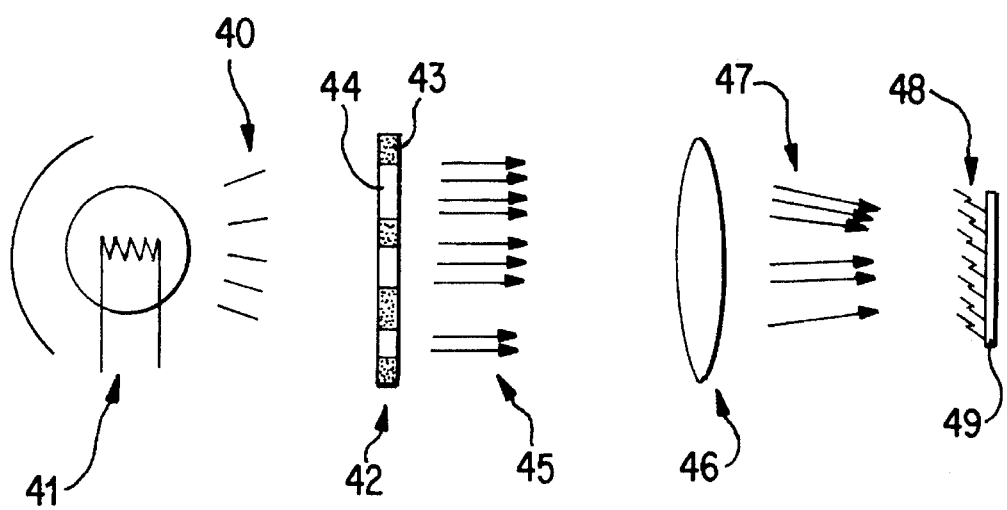
FIG. 4 shows an alternate embodiment of the invention in which a UV pattern is formed by projecting the mask pattern on the sample.

FIG. 4 is a schematic representation of an alternative arrangement in which the surface of a SAM on a substrate is exposed to a pattern of light by means of appropriate optics, such as a projection lithography configuration. UV light 40 from a UV light source 41 is directed through a mask 42 having a desired pattern of opaque portions 43 and light transparent portions 44 to form a corresponding UV light exposure pattern or image 45. Light image 45 is then directed through an optical system 46 to produce a focused image 47. The optical system 46 directs image 47 onto a SAM 48 formed on a substrate 49 in air, whereby the thiolate head groups in the exposed areas of the monolayer are oxidized to sulfonate groups. The molecules in the exposed areas can then be exchanged for other thiolate molecules as described above.

By judicious choice of the alkylthiol molecules, the process according to the invention can be used to define regions on a surface that will strongly promote and retard the adsorption of selected biological molecules. Thus, the pattern monolayer acts as a molecular template to direct the adsorption of biomolecules on the surface.

For example, the foregoing technique can be used to deposit a protein on a molecular surface in accordance with a predetermined micropattern. Using the techniques of ellipsometry and contact angle wetting, it was established that a protein adsorbs strongly to carboxylic acid-terminated thiol monolayers and very little to perfluorinated thiol monolayers. Thus, by creating a pattern of carboxylic acid monolayer in a perfluorinated monolayer (or vice versa), and then immersing the sample in a protein solution, the protein can be made to "stick" on the parts of the surface that contain only the carboxylic acid groups.

The surfaces of the thiolate SAMs can be designed to effect either specific or nonspecific binding of biological molecules. Specific binding is a strong and specific interaction without covalent bonding between two species such as proteins-receptors, enzymes-substrates, antibodies-antigens and DNA-oligonucleotide probes. Specific binding involves molecular recognition or "handshaking" and may be thought of in terms of a lock and key model where a molecule fits snugly into a quasi-depression or molecular pocket of its binding partner. Numerous interactions between different functional groups may account for the coupling. One example of specific binding is biotin-avidin coupling. Avidin, a large protein, has four separate binding cavities that will each accommodate one biotin molecule. The binding of biotin by avidin is very strong and highly specific. Another well known example of specific binding is the zipping together of one strand of DNA with another or hybridization of a DNA strand with a complementary oligonucleotide probe.

Specific binding can be used to selectively attach DNA probes to SAM surfaces which have been UV-photopatterned. The patterning of large arrays of different DNA probes on a microchip surface is useful in applications involving DNA sequencing or clinical diagnosis of genetic or infectious diseases. The patterned arrays of probes are exposed to an unknown sample of DNA to be analyzed, and the chip can then detect and readout which if any of the probes in the patterned array has bound the unknown DNA sample. From this information it is possible to derive useful information about the sequence of the unknown DNA or in diagnostic applications to verify the presence of DNA sequences which are characteristic of genetic diseases or indicative of the presence of DNA of viruses or bacteria.

Nonspecific binding can be very strong but normally lacks the shape selectivity and multiple interactions of different functional groups associated with specific binding. An example of nonspecific binding is the adsorption of avidin on carboxylic-acid terminated SAMs. The interaction in such a case is believed to be primarily electrostatic. The avidin molecule has a net positive charge, while the carboxy-terminated SAM has a net negative charge, so that the two will attract each other. The binding is nonspecific because any protein or other molecule possessing a net positive charge will bind to the SAM surface.

The steps performed in depositing a protein pattern, as described above, are illustrated in FIGS. 5a–5c. In FIG. 5a, a SAM of perfluorinated thiol 1 is formed on a gold surface. The perfluorinated SAM is then irradiated with photopatterned ultraviolet light, as shown in FIG. 5b, and the UV exposed perfluorinated SAM is immersed in a solution of carboxylic acid-terminated thiol 2. Thiol 2 adsorbs in the regions that were exposed to the UV light, as shown in FIG. 5c. In the unexposed areas perfluorinated thiol 1 is retained, and a patterned SAM is thus produced, comprised of thiol 1 and thiol 2. Finally, as shown in FIG. 5d, the patterned SAM is immersed in a solution of protein, which adsorbs only to the regions of the surface containing the carboxylic acid-terminated thiol 2, resulting in the patterning of the protein surface.

The foregoing general strategy of manipulating the chemical reactivity of surfaces via the photopatterning process to direct the placement of biomolecules on surfaces may be applicable to a wide variety of biological molecules and/or cells. In addition, the same process may be used to pattern multiple biological species by repeating the second through the fourth steps. A schematic of such a system is shown in FIG. 6. The ability to fabricate arrays of different biological species on surfaces with micron resolution has important technological potential for biosensing and diagnostic procedures. The advantages of such biosensing arrays in diagnostics include low cost, small size, and most importantly, the ability to perform hundreds of diagnostic tests on a single small test sample.

Finally, it is noted that the patterned monolayers according to the invention can also act as resists for the selective chemical etching of substrates, whereby the exposed areas of the substrate are attacked and dissolved by the chemical etch, while the unexposed monolayers areas protect the substrate from the etch.

Further details of the invention will become apparent from the following specific examples, which are intended to be merely illustrative and are not considered to limit the scope of the invention.

EXAMPLE 1

In a first example of the application of the process according to the invention, a SAM was first formed on a substrate comprising a 200 nm silver film sputter deposited on a polished silicon chip by immersing the substrate in an approximately 1 mM solution of mercaptoundecanoic acid in ethanol. Next, a 400 mesh electron microscopy grid was placed over the SAM on the substrate and the resulting assembly was irradiated for 1 hour with UV light from a mercury vapor lamp. The sample thereafter was immersed in an approximately 1 mM solution of octanethiol in ethanol, whereby the sulfonylundecanoic acid molecules which had formed in the exposed areas were exchanged for octanethiolate molecules. Subsequent analysis by SIMS imaging showed that a patterned image was formed in which features as small as 20 μm were easily recognizable.

EXAMPLE 2

A SAM of perfluorodecanethiol [$CF_3(CF_2)_7(CH_2)_2SH$] was formed on a gold substrate. The resulting thiolate monolayer was then exposed through a 300 mesh electron microscopy grid for one hour to UV light from a mercury vapor lamp, after which the exposed substrate was immersed for one hour in a 1 mM solution of mercaptoundecanoic acid [$HOOC(CH_2)_{10}SH$] in ethanol to obtain a patterned SAM comprised of squares of carboxydecanethiolate in a grid of perfluorodecanethiolate. The patterned SAM was immersed in a solution of the protein, avidin, and the avidin adsorbed to the areas of the SAM composed of the carboxy-terminated thiolate.

Figure 7A:
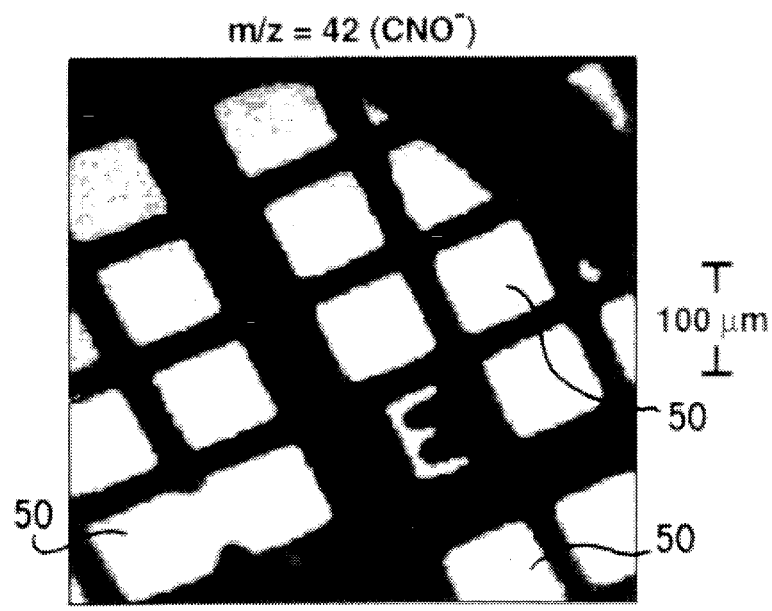
FIGS. 7a–7b show SIMS images of a biological molecule adsorbed on a surface.
Figure 7B:
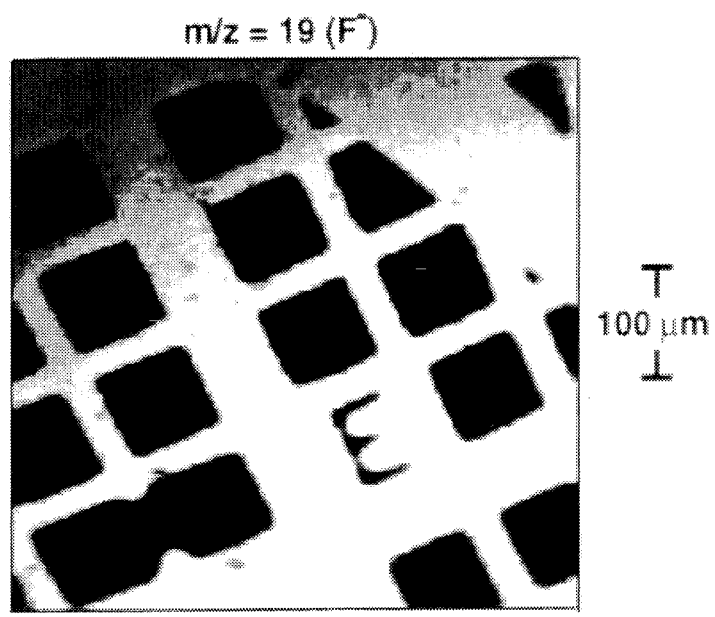

The molecular composition of the avidin patterned sample was then mapped by means of SIMS imaging. A SIMS image of the sample treated according to the process set forth above is shown in FIGS. 7a and 7b. The image of FIG. 7a is from $CNO^-$ (mass 42) which originates from the polypeptide backbone of the protein. The bright areas 50 represent regions where intense $CNO^-$ signals are detected. These regions correspond to the locations where the mercaptoundecanoic acid has patterned into the perfluorinated decanethiol 2 monolayer. The image in FIG. 7b is from $F^-$ (mass 19) and was acquired from the same area as that of the $CNO^-$ image. It demonstrates that perfluorinated thiol occupies regions where little avidin has adsorbed.

EXAMPLE 3

A SAM of decanethiol molecules on a silver-coated substrate is exposed to a desired pattern of ultraviolet light in an ambient air atmosphere to convert the thiolate groups in the exposed areas to sulfonate groups. The exposed monolayer is then immersed in a solution of a carboxylic acid-terminated alkylthiol compound so that a carboxylic acid terminated SAM is patterned into the exposed areas of the decanethiolate monolayer. A 9-mer DNA probe comprising a defined sequence of nine nucleotides is then covalently coupled to the carboxy-terminated regions. The substrate can then be exposed to a solution containing a DNA sample to be tested for the presence of a sequence complementary to the probe. If DNA having a complementary sequence is present, it will specifically bind to the probe areas of the substrate. This procedure is particularly useful to test for the presence of specific genetic defects.

Although the invention has been described and illustrated in detail, it is to be clearly understood that the same is by way of illustration and example, and is not to be taken by way of limitation. Since modifications of the disclosed embodiments incorporating the spirit and substance of the invention may occur to persons skilled in the art, the invention should be construed to include everything within the scope of the appended claims and equivalents thereof.

What is claimed is:

1. A process for creating a pattern comprising a two dimensional spacial distribution of thiolate compound molecules in a self-assembled monolayer formed on a substrate, said process comprising the steps of:

illuminating a surface of a self-assembled monolayer of a first thiolate compound in the presence of oxygen with high frequency electromagnetic radiation, distributed according to a desired pattern; and immersing said substrate in a solution of a compound which forms a second thiolate compound, whereby molecules of said first thiolate compound in illuminated areas of said monolayer are exchanged for molecules of said second thiolate compound.

2. A process according to claim 1, wherein said illuminating step is carried out in air.

3. A process according to claim 1, wherein said step of illuminating comprises:

placing a mask over said surface of said self assembled monolayer, said mask having radiation transmitting and radiation blocking portions distributed according to said desired pattern, and;

projecting said radiation through said radiation transmitting portions onto the surface of the self-assembled monolayer.

4. A process according to claim 1, wherein said step of illuminating comprises projecting said desired pattern of radiation onto the surface of the self-assembled monolayer through an optical focussing element.

5. A process according to claim 1, wherein said step of illuminating comprises illuminating said surface of said self-assembled monolayer with light from a high pressure mercury vapor lamp.

6. A process according to claim 1, wherein said substrate is selected from the group consisting of gold, silver, copper, platinum, iridium, palladium, rhodium, mercury, osmium, ruthenium, gallium arsenide, indium phosphide, and mercury cadmium telluride.

7. A process according to claim 1, wherein said step of illuminating comprises illuminating said surface of said self-assembled monolayer with UV light or X-ray radiation.

8. A process for controlling chemical and physical properties of selected areas of a surface capable of forming a thiol self-assembled monolayer according to a predetermined pattern, said process comprising the steps of:

forming a self-assembled monolayer of a first thiolate compound on said surface;

exposing said self-assembled monolayer in the presence of oxygen to electromagnetic radiation distributed according to said predetermined pattern, said electromagnetic radiation selected from the group consisting of ultra violet and x-ray radiation; and immersing the self-assembled monolayer in a solution of a compound which forms a second thiolate compound different from said first thiolate compound.

9. A process according to claim 8, wherein said exposing step comprises:

placing a mask over said surface of said self assembled monolayer, said mask having radiation transmitting portions and radiation blocking portions distributed according to said desired pattern, and projecting said radiation through said radiation transmitting portions onto the surface of the self-assembled monolayer.

10. A process according to claim 8 wherein said exposing step comprises projecting said desired pattern of radiation onto the surface of the self-assembled monolayer through optical focussing element.

11. A process according to claim 8, wherein said exposing step is carried out in air.

12. A process for selectively applying biological molecules to a surface, comprising the steps of:

forming on said surface a self assembled monolayer of a first thiolate compound;

exposing said self-assembled monolayer in the presence of oxygen to high frequency radiation which promotes oxidation of thiolate groups to sulfonate groups; said radiation being distributed according to a desired pattern of said biological molecules;

immersing the exposed self-assembled monolayer in a solution of a compound which forms a second thiolate compound;

wherein said biological molecule preferentially adsorbs on onto one of the said first and second thiolate compounds; and immersing the exposed self-assembled monolayer in a solution of said biological molecule.

13. A process according to claim 12, wherein one of the thiolate compounds has a strong affinity for adsorbing said biological molecule and the other thiolate compound has essentially no affinity for adsorbing said biological molecule.

14. A process according to claim 12, wherein said first thiolate compound is a perfluorinated alkylthiolate; said second thiolate compound is carboxylic acid-terminated alkylthiolate, and said biological molecule is a protein.

15. A process according to claim 12, wherein said first and second thiolate compounds each comprise a different oligonucleotide group, and said biological molecule is a DNA strand comprising a nucleotide sequence complementary to one of said different oligonucleotide groups.

* * * * *